(12) United States Patent
Yoshimachi

(10) Patent No.: US 9,044,574 B2
(45) Date of Patent: Jun. 2, 2015

(54) CATHETER

(71) Applicant: ASAHI INTECC CO. LTD., Nagoya-shi, Aichi (JP)

(72) Inventor: Fuminobu Yoshimachi, Aomori (JP)

(73) Assignee: ASAHI INTECC CO., LTD., Nagoya (JP)

( * ) Notice: Subject to any disclaimer, the term of this patent is extended or adjusted under 35 U.S.C. 154(b) by 125 days.

(21) Appl. No.: 13/940,787

(22) Filed: Jul. 12, 2013

(65) Prior Publication Data

US 2014/0039464 A1      Feb. 6, 2014

(30) Foreign Application Priority Data

Aug. 6, 2012   (JP) .................................. 2012-174384

(51) Int. Cl.
*A61M 25/00*   (2006.01)

(52) U.S. Cl.
CPC ....... *A61M 25/0053* (2013.01); *A61M 25/0012* (2013.01); *A61M 25/0041* (2013.01); *A61M 25/005* (2013.01); *A61M 25/007* (2013.01); *A61M 2025/0042* (2013.01)

(58) Field of Classification Search
USPC ......................................................... 604/525
See application file for complete search history.

(56) References Cited

U.S. PATENT DOCUMENTS

| | | | |
|---|---|---|---|
| 4,117,836 A * | 10/1978 | Erikson ......................... | 600/435 |
| 4,405,314 A | 9/1983 | Cope | |
| 5,476,453 A * | 12/1995 | Mehta ........................... | 604/532 |
| 6,280,434 B1 * | 8/2001 | Kinoshita et al. ............. | 604/530 |
| 8,518,011 B2 * | 8/2013 | Goodson et al. .............. | 604/508 |
| 2009/0192494 A1 | 7/2009 | Michishita et al. | |
| 2011/0190708 A1 * | 8/2011 | Shaked et al. ................. | 604/180 |

FOREIGN PATENT DOCUMENTS

| | | |
|---|---|---|
| EP | 0 959 929 B1 | 1/2005 |
| EP | 1 504 784 A1 | 2/2005 |
| JP | A-2002-186670 | 7/2002 |
| WO | WO 98/33544 A1 | 8/1998 |
| WO | WO 2007/111244 A1 | 10/2007 |

OTHER PUBLICATIONS

Oct. 7, 2013 European Search Report issued in EP 13 17 2991.5.
Nov. 5, 2014 Notification of Refusal issued in Japanese Patent Application No. 2012-174384 (with English Translation).

* cited by examiner

*Primary Examiner* — Nicholas Lucchesi
*Assistant Examiner* — Diva K Chander
(74) *Attorney, Agent, or Firm* — Oliff PLC

(57) ABSTRACT

A catheter includes a first opening portion positioned at a distal end; a first curved portion positioned proximally of the first opening portion, and is curved in a first direction; a second curved portion positioned proximally of the first curved portion, and is curved in a second direction; an intermediate portion provided between the first curved portion and the second curved portion; and a second opening portion formed in the intermediate portion. In a transverse sectional view of the intermediate portion, the first direction and the second direction are directions directed towards a first side of the intermediate portion. In addition, in the transverse sectional view of the intermediate portion, the second opening portion opens in a third direction directed towards a second side of the intermediate portion that is opposite to the first side.

9 Claims, 8 Drawing Sheets

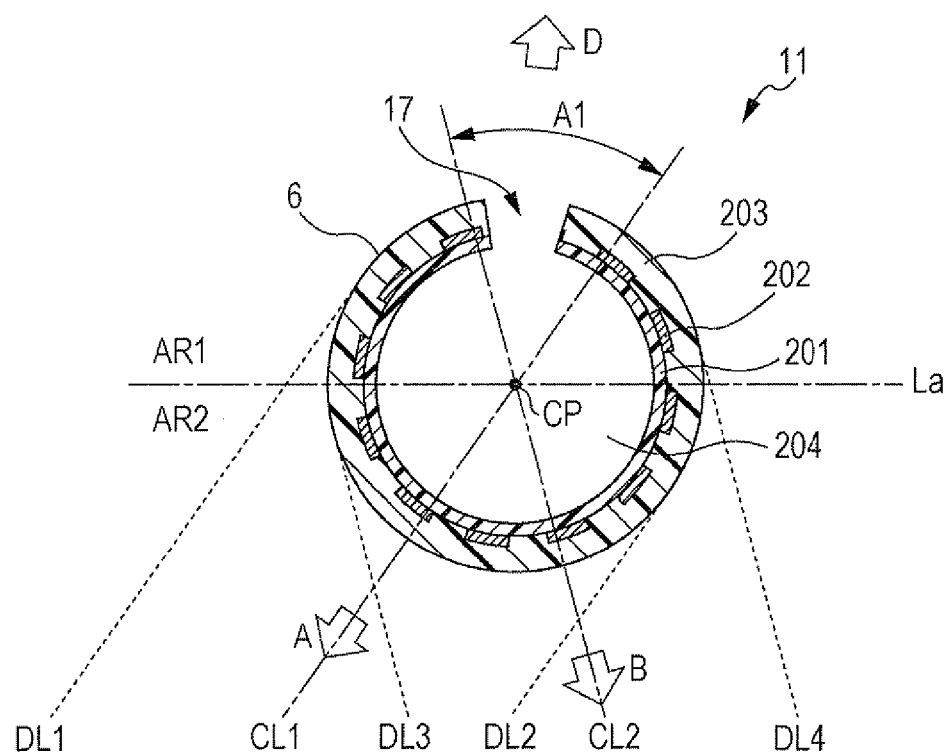
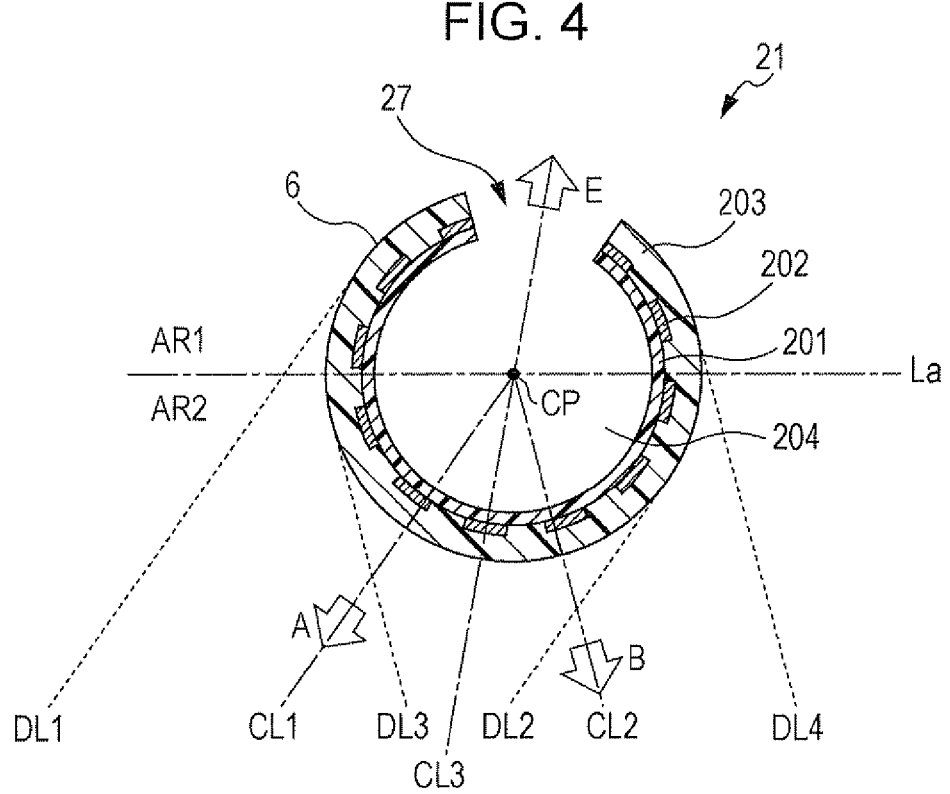

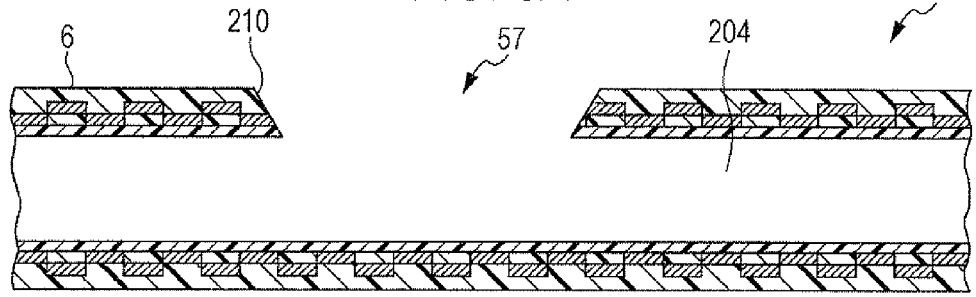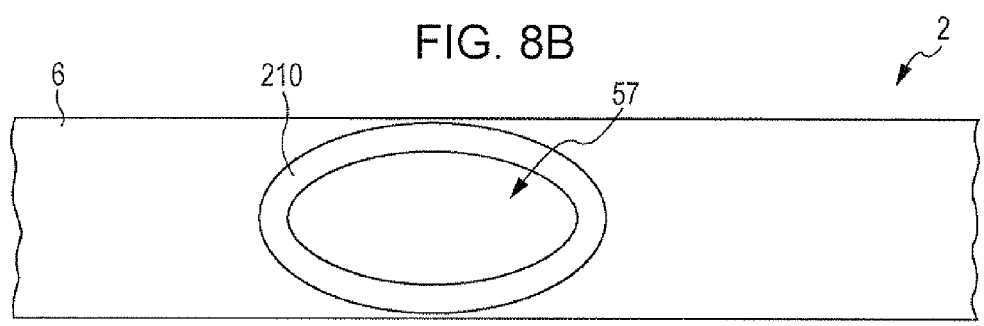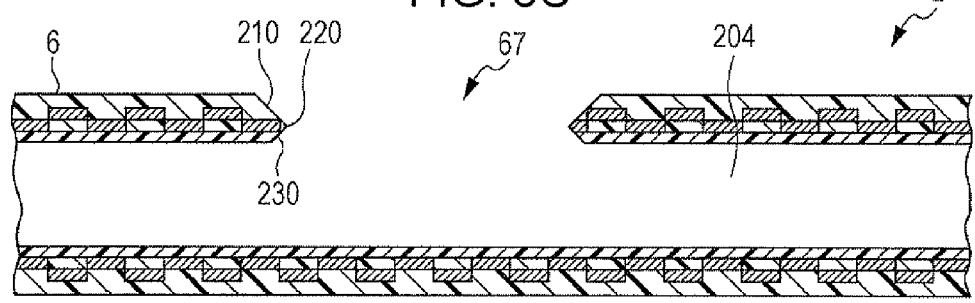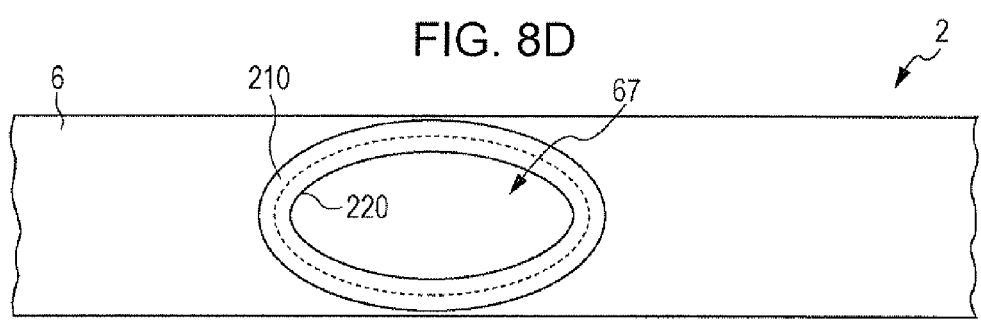

CATHETER

CROSS REFERENCE TO RELATED APPLICATION

This application claims priority to Japanese Patent Application No. 2012-174384 filed in the Japan Patent Office on Aug. 6, 2012, the entire contents of which are incorporated herein by reference.

BACKGROUND

1. Field

The disclosed embodiments relate to a medical device. Specifically, the disclosed embodiments related to a catheter.

2. Description of Related Art

In recent years, various catheters used in internal treatments/examinations of lesions in blood vessels including coronary arteries, internal treatments/examinations of lesions in vessels other than blood vessels, and internal treatments/examinations of lesions of kidneys have been proposed.

For example, Domestic Re-publication of PCT International Publication for Patent Application No. WO2007/111244 (Cited Document 1) describes a catheter that is to be disposed in the coronary sinus. A shaft at a distal end of the catheter includes a first linear portion, a first curved portion that is formed continuously with a distal end side of the first linear portion, a second curved portion that is formed continuously with a distal end side of the first curved portion and that is curved in a direction directed towards a side that is opposite to the side towards which the first curved portion curves, a second linear portion that is formed continuously with a distal end side of the second curved portion, a third curved portion that is formed continuously with a distal end side of the second linear portion and that is curved in a direction directed towards a side that is opposite to the side towards which the second curved portion curves, and a third linear portion that is formed continuously with a distal end side of the third curved portion. The catheter has at least one opening having a diameter of at least 1.8 mm and is disposed closer to a distal end of the catheter than an apex of the second curved portion.

Japanese Unexamined Patent Application Publication No. 2002-186670 (Cited Document 2) discusses a catheter for contrastradiography of a coronary artery, which includes a main tube and a pigtail loop portion that is provided at a distal end of the main tube via an angle portion. The main tube has a plurality of side holes.

U.S. Pat. No. 4,405,314 (Cited Document 3) discusses a catheter that is inserted into a pelvis of the kidney, and that includes a curved portion at a distal end portion of the catheter. A distal end side of the curved portion has a side hole.

SUMMARY

In particular, among internal treatments using catheters, treatments of occluded portions of coronary arteries are increasing. In addition, in recent years, due to advances in medical technology, a chronic total occlusion (CTO) lesion that completely occludes a blood vessel can be treated.

CTO is a lesion in which a left coronary artery is completely occluded and occurs when the left coronary artery is gradually occluded over a long period of time. When a person contracts CTO in the left coronary artery, blood is carried into a blood vessel that is situated closer to a periphery than the blood vessel that is completely occluded by CTO. Therefore, a blood vessel is newly grown from, for example, a right coronary artery, and is connected to the periphery of the left coronary artery, as a result of which a collateral circulation path is often formed.

In order to treat CTO of a left coronary artery, a total of two catheters is used. They are a catheter for a left coronary artery and a catheter for a right coronary artery. The catheter for a left coronary artery is used for treating CTO of the left coronary artery. The catheter for a right coronary artery is used for performing contrastradiography of the left coronary artery, which is situated closer to the periphery than is a CTO lesion, via a collateral circulation path as a result of injecting contrast medium from a right coronary artery. Such contrastradiography is hereunder referred to as "contralateral contrastradiography".

When two catheters are inserted at the same time into the entrance of a coronary artery, the catheters interfere with each other, as a result of which it is difficult to stably dispose the catheters. Therefore, this has prolonged the treatment of CTO. Because of this, in medicine, there has been a strong demand for one catheter that is capable of efficiently performing treatment of CTO of one of the coronary arteries and contralateral contrastradiography on the other blood vessel.

The catheters according to the Cited Documents 1 to 3 each have an opening portion at the distal end, and a side hole located proximally of the opening portion. However, even if the opening portion is inserted into the entrance of one of the coronary arteries, the catheter cannot be used in the aforementioned CTO treatment because the side hole opens in a direction that differs from the direction of the entrance of the other coronary artery.

Accordingly, in view of such a problem, the disclosed embodiments provide a catheter having an opening portion that is provided closer to a proximal end than to a distal end of the catheter, and that, with a distal end of the catheter being inserted in the entrance of one of the coronary arteries, opens in the direction of the entrance of the other coronary artery.

According to the disclosed embodiments, there is provided a catheter including a first opening portion that is positioned at a distal end; a first curved portion that is positioned proximally of the first opening portion, and that is curved in a first direction; a second curved portion that is positioned proximally of the first curved portion, and that is curved in a second direction; an intermediate portion that is provided between the first curved portion and the second curved portion; and a second opening portion that is formed in the intermediate portion. In a transverse sectional view of the intermediate portion, the first direction and the second direction are directions directed towards a first side of the intermediate portion. In addition, in the transverse sectional view of the intermediate portion, the second opening portion opens in a third direction directed towards a second side of the intermediate portion that is opposite to the first side.

In the present specification, in a transverse sectional view of the intermediate portion, the first direction corresponds to a direction towards which the first curved portion faces, and the second direction corresponds to a direction towards which the second curved portion faces.

The phrase "the first direction and the second direction are directions directed towards a first side" means that, in transverse sectional view of the intermediate portion, the first and second directions are directed towards an upward side or a downward side.

The phrase "a third direction directed towards a second side that is opposite to the first side" means that, in the transverse sectional view of the intermediate portion, a third direction directed towards the second side is directed towards a downward side when the first direction and the second direction are directed towards an upward side, or directed towards an upward side when the first direction and the second direction are directed towards a downward side.

The aforementioned "first direction", "second direction", "directions directed towards a first side", and "a third direction directed towards a second side that is opposite to the first side" are described in detail below with reference to the drawings.

In the disclosed embodiments, even in a state in which the first opening portion is inserted in the entrance of one of the coronary arteries, the second opening portion opens towards the entrance of the other coronary artery. Consequently, when a microcatheter is disposed in the other coronary artery through the second opening portion, it is possible to perform treatment of a lesion of one of the coronary arteries and perform contralateral contrastradiography of the other coronary artery using one catheter. Thus, it is possible to increase the efficiency with which percutaneous coronary intervention (PCI) operation is performed.

BRIEF DESCRIPTION OF THE DRAWINGS

FIG. 3 is a transverse sectional view of a second opening portion of a catheter according to a second embodiment.

FIG. 4 is a transverse sectional view of a second opening portion of a catheter according to a third embodiment.

FIGS. 8A to 8D are vertical sectional views and plan views of catheters showing modifications, with FIG. 8A being a vertical sectional view of a modification of the second opening portion, FIG. 8B being a plan view of FIG. 8A, FIG. 8C being a vertical sectional view of another modification, and FIG. 8D being a plan view of FIG. 8C.

DETAILED DESCRIPTION

Various embodiments of a catheter will hereunder be described with reference to the drawings.

Figure 1A:
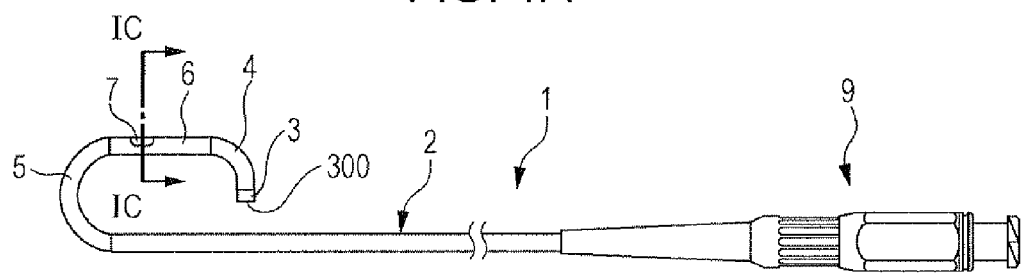
FIGS. 1A to 1C each illustrate the structure of a catheter according to a first embodiment, with FIG. 1A illustrating the entire catheter, FIG. 1B being a plan view of FIG. 1A, and FIG. 1C being a transverse sectional view of the catheter taken along line IC-IC in FIG. 1A.
Figure 1B:
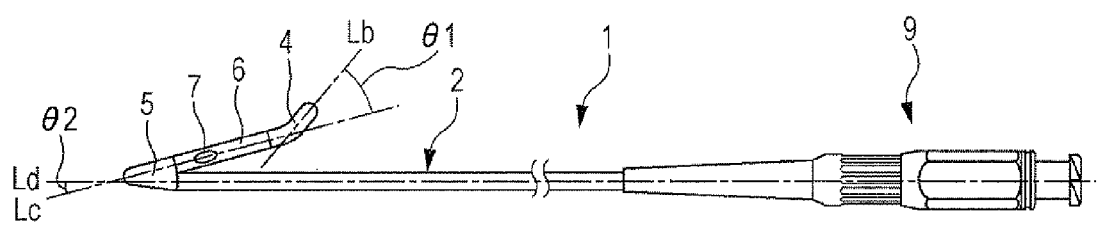
Figure 1C:
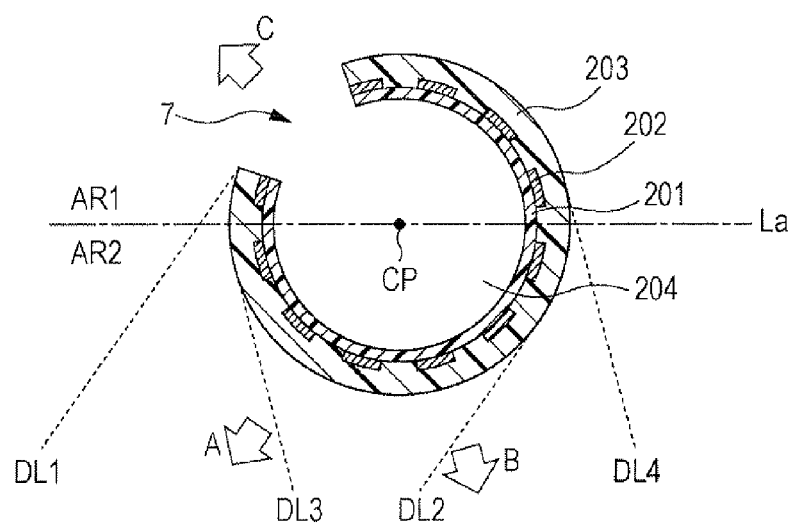

FIGS. 1A to 1C each illustrate the structure of a catheter 1 according to a first embodiment, with FIG. 1A illustrating the entire catheter 1, FIG. 1B being a plan view of FIG. 1A, and FIG. 1C being a transverse sectional view of the catheter 1 taken along line IC-IC in FIG. 1A.

In order to facilitate understanding, in FIGS. 1A and 1B, the entire catheter 1 is schematically shown, with the catheter 1 being shortened in a lengthwise direction thereof. Therefore, the overall dimensions differ from the actual dimensions.

In FIGS. 1A and 1B, from the side of a proximal end (that is, the right side in FIGS. 1A and 1B) of the catheter 1, the catheter 1 includes a connector 9 and a catheter body 2 that is positioned at a distal end of the connector 9. The interior of the catheter 1 is provided with a lumen 204 (see FIG. 1C) that extends from a proximal end of the connector 9 to a first opening portion 300 of a distal-end tip 3 that is positioned at a tip portion of the catheter body 2.

Unless otherwise specified, the description below is given with the side where the distal-end tip 3 is disposed being defined as the side of the distal end of the catheter 1, and the side where the connector 9 is provided being defined as the side of the proximal end of the catheter 1.

The catheter body 2 includes the lumen 204, the distal-end tip 3, a first curved portion 4, a second curved portion 5, an intermediate portion 6, and a second opening portion 7. The lumen 204 extends over the entire length of the catheter body 2 in the interior of the catheter body 2. The distal-end tip 3 forms the tip portion of the catheter body 2 and has the first opening portion 300 that is positioned at a tip portion of the lumen 204. The first curved portion 4 is positioned proximally of the first opening portion 300. The second curved portion 5 is positioned at proximally of the first curved portion 4. The intermediate portion 6 is provided between the first curved portion 4 and the second curved portion 5. The second opening portion 7 is formed in the intermediate portion 6. The catheter 1 has an overall length of 800 mm to 1500 mm, an outside diameter of 1.3 mm to 3.0 mm, and an inside diameter of 1.0 mm to 2.5 mm.

For facilitating understanding and for convenience, FIG. 1B shows a line segment Lb passing through the center of a portion of the first curved portion 4, a centerline Lc of the intermediate portion 6 of the catheter 1, and a centerline Ld of a proximal end portion of the catheter body 2 that is connected to the connector 9.

In FIGS. 1A and 1B, the first curved portion 4 is formed with respect to the intermediate portion 6 so that an angle that is formed by the line segment Lb of the first curved portion 4 and the centerline Lc of the intermediate portion 6 becomes θ1. Further, the second curved portion 5 is formed with respect to the intermediate portion 6 so that an angle that is formed by the centerline Lc of the intermediate portion 6 and the centerline Ld of the catheter body 2 is θ2.

Next, the structure of the catheter body 2 is described with reference to FIG. 1C. FIG. 1C is a transverse sectional view of the intermediate portion 6 having the second opening portion 7 taken along line IC-IC in FIG. 1A. The catheter body 2 includes an inner layer 201, a reinforcing body 202, and an outer layer 203. The inner layer 201 is formed of resin. The reinforcing body 202 covers the inner layer 201 and provides rigidity to the catheter body 2. The outer layer 203 covers the inner layer 201 and the reinforcing body 202, and is formed of resin. The structure of the catheter body 2 is the same from a distal end towards a proximal end of the first curved portion 4.

The distal-end tip 3, which is formed at the tip portion of the catheter body 2, has a cylindrical shape and is formed of a resin that is more flexible than the resin of which the outer layer 203 of the catheter body 2 is formed.

Next, a first direction of the first curved portion 4, a second direction of the second curved portion 5, and the relationship between the position of the second opening portion 7 and these directions are described with reference to FIG. 1C. In the embodiment, the first direction of the first curved portion 4 refers to the direction in which the first curved portion 4 is curved in transverse sectional view of the intermediate portion 6. In addition, the second direction of the second curved portion 5 refers to the direction in which the second curved portion 5 is curved in transverse sectional view of the intermediate portion 6.

In FIG. 1C, in transverse sectional view of the intermediate portion 6, a line segment La that passes through a center point CP of the catheter body 2 and that bisects the transverse section into an upper section (AR1 side) and a lower section (AR2 side) is illustrated. In FIG. 1C, the first curved portion 4 is curved so as to be positioned between a broken line DL1 and a broken line DL2, respectively, in transverse sectional view of the intermediate portion 6 of the catheter 1. Therefore, the first direction of the first curved portion 4 is an obliquely leftward direction (that is, the direction of arrow A) at the AR2 side in transverse sectional view of the intermediate portion 6.

The second curved portion 5 is curved so as to be positioned between a broken line DL3 and a broken line DL4, respectively. Therefore, the second direction of the second curved portion 5 is an obliquely rightward direction (that is, the direction of arrow B) at the AR2 side in transverse sectional view of the intermediate portion 6.

That is, the first and second directions are directions directed towards the same side (that is, the AR2 side).

In FIG. 1C, the second opening portion 7 is provided so as to face an obliquely leftward direction (that is, the direction of arrow C) in transverse sectional view of the intermediate portion 6 of the catheter 1, and is connected to the lumen 204 of the catheter 1. An opening direction of the second opening portion 7 (that is, the direction of arrow C (AR1 side)) is directed towards the side that is opposite to the side towards which the first direction (that is, the direction of arrow A (AR2 side)) and the second direction (that is, the direction of arrow B (AR2 side)) are directed.

Next, the forms of use of the catheter 1 and the advantages that are provided when the catheter 1 according to the embodiment is used are described with reference to FIG. 2.

Figure 2:
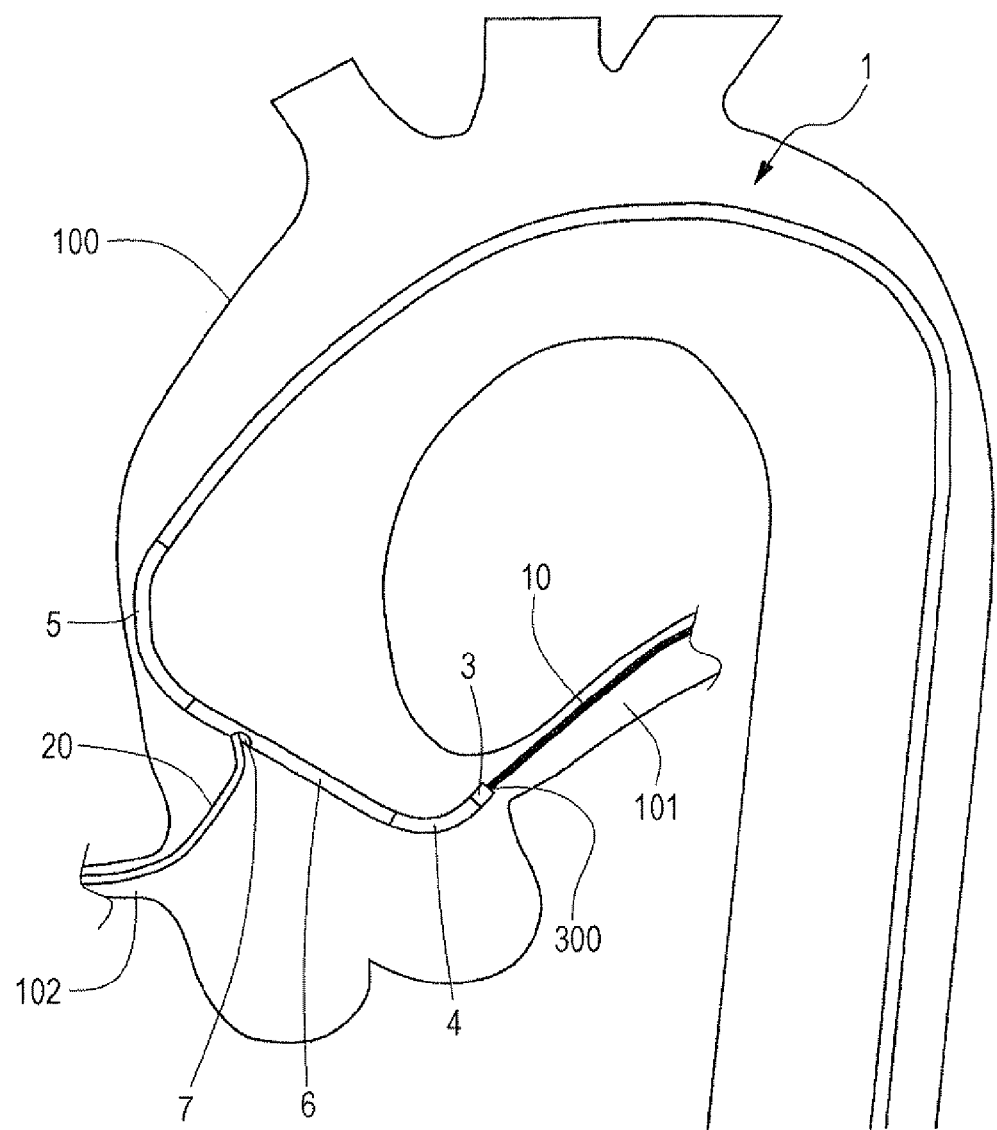
FIG. 2 is an explanatory view of a state in which the catheter according to the first embodiment is used.

FIG. 2 shows the insertion of the distal end (that is, the first opening portion 300) of the catheter 1 into a left coronary artery 101 when it is assumed that an obstructing lesion (not shown) exists in the left coronary artery 101. The catheter 1 is inserted from a patient's femoral artery, and is passed through an aorta 100, to insert the distal end (that is, the first opening portion 300) of the catheter 1 into the left coronary artery 101. A first medical device 10, such as a guidewire, is inserted into the left coronary artery 101 through the first opening portion 300.

In this state, a second medical device 20, such as a microcatheter, is inserted into a right coronary artery 102 through the second opening portion 7. By causing a contrast medium to flow into the right coronary artery 102 through the microcatheter, it is possible to perform contralateral contrastradiography.

Accordingly, the catheter 1 according to the embodiment includes the intermediate portion 6, which is disposed between the first curved portion 4 and the second curved portion 5, and the second opening portion 7, which is formed in the intermediate portion 6. In addition, as described above, the second opening portion 7 opens in a direction directed towards a side that is opposite to the side towards which the first direction of the first curved portion 4 and the second direction of the second curved portion 5 are directed in transverse sectional view of the intermediate portion 6. Therefore, even if the first opening portion 300 is inserted in the entrance of one of the coronary arteries (that is, the left coronary artery 101 in FIG. 2), since the second opening portion 7 opens towards the entrance of the other coronary artery (that is, the right coronary artery 102 in FIG. 2), when a microcatheter is disposed in the other coronary artery through the second opening portion 7, it is possible to perform treatment of a lesion of one of the coronary arteries and perform contralateral contrastradiography of the other coronary artery using one catheter.

Since such treatments are performed using one catheter, it is possible to reduce the burden on a patient during treatment and after treatment. In addition, since it is not necessary to use two catheters at the same time, it is possible to reduce the time taken for operations, and to increase the efficiency of PCI operations.

Further, when a medical device, such as a balloon catheter or a stent, is inserted into the left coronary artery 101 through the interior of the catheter 1, the catheter 1 is sometimes subjected to a force that pushes it from the proximal end towards the distal end. The force that the catheter 1 receives can be dispersed in the left coronary artery 101 and in the right coronary artery 102 through the first medical device that has been inserted from the first opening portion 300 and the second medical device 20 that has been inserted from the second opening portion 7. Therefore, it is possible to stabilize the form of insertion of the catheter 1 into the left coronary artery 101.

The position where the second opening portion 7 is disposed with respect to the catheter body 2 in a long-axis direction thereof is not particularly limited. However, if insertability of a medical device, such as a microcatheter, into the entrance of the other coronary artery through the second opening portion 7 is considered, as shown in FIGS. 1A and 2, it is desirable that the second opening portion 7 be closer to the proximal end, that is, closer to the second curved portion 5 than an intermediate position (not shown) of the intermediate portion 6 is in the direction of a long axis of the intermediate portion 6. When the second opening portion 7 is disposed at such a position, it becomes easier to insert a medical device, such as a microcatheter, into the other coronary artery and to perform contralateral contrastradiography of the other coronary artery.

The shape of the second opening portion 7 is not particularly limited. However, if insertability of a medical device, such as a microcatheter, into the entrance of the other coronary artery through the second opening portion 7 is considered, it is desirable that the second opening portion 7 be circular. If passability of a medical device, such as a microcatheter, through the second opening portion 7 is considered, it is desirable that the diameter of the second opening portion 7 be not less than 1 mm. Although the maximum size is not particularly limited, it is necessary to set the maximum size by considering the mechanical strength of the catheter 1 near the second opening portion 7.

Although, in FIG. 1C, the second opening portion 7 opens in the direction of arrow C towards the AR1 side, the second opening portion 7 may open in any direction as long as the second opening portion 7 opens towards the AR1 side.

The materials of the structural portions of the catheter 1 are as follows.

The inner layer 201 may be formed of, for example, fluorocarbon resin, such as polytetrafluoroethylene (PTFE), or polyolefin resin, such as high-density polyethylene (HDPE). The inner layer 201 that is formed of such a resin has low friction resistance. This makes it easier for a medical device, such as a microcatheter, to pass smoothly through the lumen 204 of the catheter 1, which is desirable.

The reinforcing body 202 may be formed of, for example, a stainless steel wire (such as an austenitic stainless steel wire or a martensitic stainless steel wire), a superelastic alloy wire (such as a Ni—Ti alloy wire, a Cu—Al—Ni alloy wire, or a Cu—Zn—Al alloy wire), a piano wire, or a tungsten wire.

Examples of the materials of the outer layer 203 are various resinous materials including, for example, polyolefin (such as polyethylene, polypropylene, and polybutadiene), soft or hard polyvinyl chloride, polyurethane, epoxy resin, cycloolefin, ethylene-vinyl acetate copolymer, polyester (such as polyethylene terephthalate and polybutylene terephthalate), polyamide (such as nylon 12 or nylon 66), polyetherpolyamide, polyether block amide, polyester polyamide, ABS resin, AS resin, fluorocarbon resin, and a shape memory resin; various thermoplastic elastomer resins of, for example, a styrene type, a polyolefin type, a polyurethane type, a polyester type, a polyamide type, a polybutadiene type, a transpolyisoprene type, a fluorocarbon rubber type, and a chlorinated polyethylene type; thermosetting elastomer resins including, for example, silicone resin and vulcanized rubber; and a polymer alloy in which two or more of the aforementioned types of resins are combined.

It is desirable that the distal-end tip 3 be formed of a resin that is more flexible than the resin forming the outer layer 203, such as polyurethane elastomer that is of a soft grade.

The connector 9 may be formed of polyethylene, polypropylene, polyacetal, polyamide, polycarbonate, polysulfone, polyether ether ketone, and any of the aforementioned elastomer resins.

The catheter 1 according to the embodiment may be suitably produced by performing Steps 1 to 5 described below.

(1) Step of Producing Catheter Body 2

First, a core for a catheter is covered with a fluorocarbon resin using a dipping method or an extrusion method, and an inner layer 201 is formed around an outer surface of the core for a catheter. Then, the surface of the inner layer 201 that has been formed is treated using a naphthalene-sodium complex.

Next, a plurality of stainless steel wires are woven to the outer surface of the core for a catheter around which the inner surface 201 is formed, to form a reinforcing body 202 at the surface of the inner layer 201.

Next, using an extruding device, the surface of the inner layer 201 and the surface of the reinforcing body 202 are covered with a polyamide elastomer resin, to form an outer layer 203.

After forming the outer layer 203, both ends of the core for a catheter are pulled, to remove the core for the catheter from an inner portion of the inner layer 201. The location from which the core for a catheter has been removed is where a lumen 204 is formed. As a result, the catheter body 2 is formed.

(2) Step of Forming Distal-End Tip 3

A core wire for the distal-end tip is formed by extrusion using polyurethane elastomer that is more flexible than the outer layer 203 of the catheter body 2. After pulling out the core wire, the core wire is cut to a length that is equal to the length of the distal-end tip 3.

Next, a core bar for forming the distal-end tip 3 is inserted into a distal end of the catheter body 2.

Next, with an end surface of a proximal end of the distal-end tip 3 and an end surface of the distal end of the catheter body 2 being in contact with each other while the distal-end tip 3 is passed through the core bar, these end portions are covered with a heat shrinkable tube.

Next, after heating the heat shrinkable tube, the heat shrinkable tube shrinks. Using the shrinking force and the heat, the distal-end tip 3 is joined to the catheter body 2. Thereafter, the core bar is removed, so that the distal-end tip 3 that is joined at the distal end of the catheter body 2 is formed.

(3) Step of Forming First Curved Portion 4 and Second Curved Portion 5 of Catheter Body 2

A die including a first curved portion 4 and a second curved portion 5, which are curved towards the same side, and an intermediate portion 6, which is positioned between the first curved portion 4 and the second curved portion 5, is provided. The catheter body 2 including the distal-end tip 3 is set in this die. The die is heated to form the catheter body 2 including the first curved portion 4, the second curved portion 5, and the intermediate portion 6.

(4) Step of Bonding Connector

Before bonding the catheter body 2 and a connector 9 to each other, the connector 9 is previously formed by injection molding or extrusion. The connector 9 may be formed of one type of material. However, if the required rigidity and flexibility of each portion of the connector 9 is considered, the connector 9 may also be formed of a plurality of types of materials.

When the proximal end portion of the catheter body 2 and a distal end portion of the connector 9 are bonded to each other using a generally used adhesive, such as cyanoacrylate, the catheter body 1 is formed. When the catheter body 2 and the connector 9 are to be bonded to each other, it is necessary to prevent portions of the lumen 204 disposed at the catheter body 2 and the connector 9 from being blocked by the adhesive.

(5) Step of Forming a Second Opening Portion

A second opening portion 7 is formed in the intermediate portion 6 by forming a hole using, for example, a YAG laser or by mechanically forming a hole using, for example, a center punch in a direction directed towards the side that is opposite to the side towards which the first direction of the first curved portion 4 and the second direction of the second curved portion are directed. This causes the catheter 1 having the second opening portion 7 to be formed.

It is possible to form the catheter 1 using existing methods in addition to the above-described method. For example, a catheter body 2 whose rigidity is reduced towards its distal end may be formed, for example, by forming a reinforcing body 203 using a stainless steel wire whose outside diameter decreases towards its distal end, or by reducing the pitch between the portions of a woven reinforcing body 203 towards the distal end of the catheter body 2.

As the resin used to form the outer layer 203, it is possible to use resin having a high-grade rigidity at its proximal-end side and resin whose rigidity grade is reduced towards its distal end, to form a catheter body 2 whose rigidity is reduced towards its distal end. However, in this case, it is desirable to adjust the grades of the resins so that the rigidity of the resin that forms the distal-end tip 3 is lower than the rigidity of the resin used to form the tip portion of the catheter body 2.

When the distal-end tip 3 and the catheter body 2 are to be joined to each other, the end surfaces may be brought into contact with each other as described above. However, it is possible to join the distal-end tip 3 and the catheter body 2 to each other while one end portion is disposed so as to cover the other end portion. Publicly known methods may be used depending upon what is required.

Next, a catheter 11 according to a second embodiment is described below. FIG. 3 illustrates an intermediate portion 6 of the catheter 11 in transverse sectional view. In FIG. 3, the catheter 11 has the same form as the catheter 1 according to the first embodiment except that the position of a second opening portion 17 of the catheter 11 differs from the position of the second opening portion 7 of the catheter 1 according to the first embodiment. Portions in the second embodiment that correspond to those in the first embodiment are given the same reference numerals in FIG. 3.

In FIG. 3, in transverse sectional view of the intermediate portion 6, a first curved portion 4 is curved so as to be positioned between a broken line DL1 and a broken line DL2. Therefore, a direction of curvature of the first curved portion 4 (hereunder referred to as the "first curvature direction" in the embodiment) corresponds to the direction of arrow A on a line segment CL1 at an AR2 side. The line segment CL1 is a centerline in the first curvature direction in transverse sectional view of the intermediate portion 6.

In transverse sectional view of the intermediate portion 6, the second curved portion 5 is curved so as to be positioned between a broken line DL3 and a broken line DL4. Therefore, a direction of curvature of the second curved portion 5 (hereunder referred to as the "second curvature direction" in the embodiment) corresponds to the direction of arrow B on a line segment CL2 at the AR2 side. The line segment CL2 is a centerline in the second curvature direction in transverse sectional view of the intermediate portion 6.

The line segments CL1 and CL2 also extend from the AR2 side towards the AR1 side.

In FIG. 3, the second opening portion 17 is disposed between the line segment that linearly extends in a direction directed towards the opposite side to the side towards which the first curvature direction of the first curved portion 4 is directed (the line segment CL1 at the AR1 side) and the line segment that linearly extends in a direction directed towards the opposite side to the side towards which the second curvature direction of the second curved portion 5 is directed (the line segment CL2 at the AR1 side). That is, the second opening portion 17 is disposed in a range that is indicated by a double-headed arrow A1. The opening direction of the second opening portion 17 corresponds to the direction of arrow D directed towards the AR1 side.

As is clear from FIG. 3, the opening direction of the second opening portion 17 (that is, the direction of arrow D directed towards the AR1 side) is directed towards the side that is opposite to the side towards which the first curvature direction (that is, the direction of arrow A directed towards the AR2 side) and the second curvature direction (that is, the direction of arrow B directed towards the AR2 side) are directed.

In the embodiment, the phrase "the second opening portion 17 is disposed between the line segment CL1 and the line segment CL2 (that is, the range A1)" means that at least a portion of the second opening portion 17 is disposed between the line segment CL1 and the line segment CL2 (that is, the range A1).

As mentioned above, in transverse sectional view of the intermediate portion 6, the second opening portion 17 of the catheter 11 is provided between the line segment that linearly extends in a direction directed towards the opposite side to the side towards which the first curvature direction is directed (the line segment CL1 at the AR1 side) and the line segment that linearly extends in a direction directed towards the opposite side to the side towards which the second curvature direction is directed (the line segment CL2 at the AR1 side). That is, the second opening portion 17 is disposed in the range A1. Therefore, it becomes easier to insert a guidewire or a microcatheter into the other coronary artery from the second opening portion 17, and to make it easier for a force that is applied to the catheter 11 to be dispersed to both of the coronary arteries through the guidewire or the microcatheter, the force being generated when a medical device is inserted into the catheter 11. Therefore, it is possible to increase the efficiency of PCI operations, and, thus, to stabilize the form of disposition of the catheter 11.

In FIG. 3, if the position where the second opening portion 17 reliably opposes the entrance of the other coronary artery is considered, it is desirable that the second opening portion 17 be disposed so that a center point (not shown) of the second opening portion 17 is positioned within the range A1.

By disposing the center point (not shown) of the second opening portion 17 between the line segment CL1 and the line segment CL2 (that is, in the range A1), the second opening portion 17 more precisely opposes the entrance of the other coronary artery, and, thus, a medical device, such as a microcatheter, is more easily inserted into the entrance of the other coronary artery through the second opening portion 17.

Next, a catheter 21 according to a third embodiment is described below with reference to FIG. 4. FIG. 4 illustrates an intermediate portion 6 of the catheter 21 in transverse sectional view. In FIG. 4, the catheter 21 has the same form as the catheter 1 according to the first embodiment except that the position of a second opening portion 27 of the catheter 21 differs from the position of the second opening portion 7 of the catheter 1 according to the first embodiment. Portions in the third embodiment that correspond to those of the catheter 1 in the first embodiment are given the same reference numerals in FIG. 4.

In FIG. 4, in transverse sectional view of the intermediate portion 6, a first curved portion 4 is curved so as to be positioned between a broken line DL1 and a broken line DL2. Therefore, a direction of curvature of the first curved portion 4 (hereunder referred to as the "first curvature direction" in the embodiment) corresponds to the direction of arrow A on a line segment CL1 at an AR2 side. The line segment CL1 is a centerline in the first curvature direction in transverse sectional view of the intermediate portion 6.

In transverse sectional view of the intermediate portion 6, the second curved portion 5 is curved so as to be positioned between a broken line DL3 and a broken line DL4. Therefore, a direction of curvature of the second curved portion 5 (hereunder referred to as the "second curvature direction" in the embodiment) corresponds to the direction of arrow B on a line segment CL2 at the AR2 side. The line segment CL2 is a centerline in the second curvature direction in transverse sectional view of the intermediate portion 6.

In FIG. 4, in transverse sectional view of the intermediate portion 6, the second opening portion 27 is disposed on a line (at an AR1 side) that extends from a line segment CL3 in a direction directed towards an opposite side to the side towards which the first curvature direction of the first curved portion 4 and the second curvature direction of second curved portion 5 are directed, with the line segment CL3 passing midway between the first curvature direction of the first curved portion 4 and the second curvature direction of the second curved portion 5. The opening direction of the second opening portion 27 corresponds to the direction of arrow E along a line segment CL at the AR1 side.

As is clear from FIG. 4, the opening direction of the second opening portion 27 (that is, the direction of arrow E (AR1 side)) is directed towards the side that is opposite to the side towards which the first curvature direction (that is, the direction of arrow A (AR2 side)) and the second curvature direction (that is, the direction of arrow B (AR2 side)) are directed.

In the embodiment, the phrase "the second opening portion 27 is disposed on the line extending from the line segment CL3" means that at least a portion of the second opening portion 27 is disposed on the line extending from the line segment CL3.

As mentioned above, in transverse sectional view of the intermediate portion 6, the second opening portion 27 is disposed on the line that extends from the line segment CL3 in the direction directed towards the opposite side to the side towards which the first curvature direction of the first curved portion 4 and the second curvature direction of the second curved portion 5 are directed, with the line segment passing midway between the first curvature direction of the first curved portion 4 and the second curvature direction of the second curved portion 5. Therefore, it becomes easier to insert a guidewire or a microcatheter into the other coronary artery from the second opening portion 27, and it becomes easier for a force that is applied to the catheter 11 to be dispersed to both of the coronary arteries through the guidewire or the microcatheter, the force being generated when a medical device is inserted into the catheter 21. Therefore, it is possible to increase the efficiency of PCI operations, and, thus, to stabilize the form of disposition of the catheter.

In FIG. 4, if the position where the second opening portion 27 reliably opposes the entrance of the other coronary artery is considered, it is desirable that the second opening portion 27 be disposed so that a center point (not shown) of the second opening portion 27 is positioned on or near the line extending from the line segment CL3.

By disposing the center point (not shown) of the second opening portion 27 on the line extending from the line segment CL3, the second opening portion 27 more precisely opposes the entrance of the other coronary artery, and, thus, a medical device, such as a microcatheter, is more easily inserted into the entrance of the other coronary artery through the second opening portion 27.

Next, with reference to FIG. 5, a catheter 31 according to a fourth embodiment is described focusing on the differences between the catheter 31 according to the fourth embodiment and the catheter 1 according to the first embodiment. Portions in the fourth embodiment that correspond to those in the first embodiment are given the same reference numerals in FIG. 5.

Figure 5A:
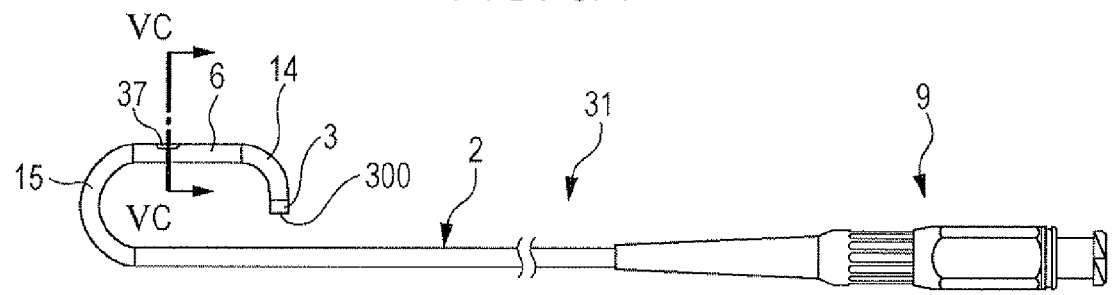
FIGS. 5A to 5C each illustrate the structure of a catheter according to a fourth embodiment, with FIG. 5A illustrating the entire catheter, FIG. 5B being a plan view of FIG. 5A, and FIG. 5C being a transverse sectional view of the catheter taken along line VC-VC in FIG. 5A.
Figure 5B:
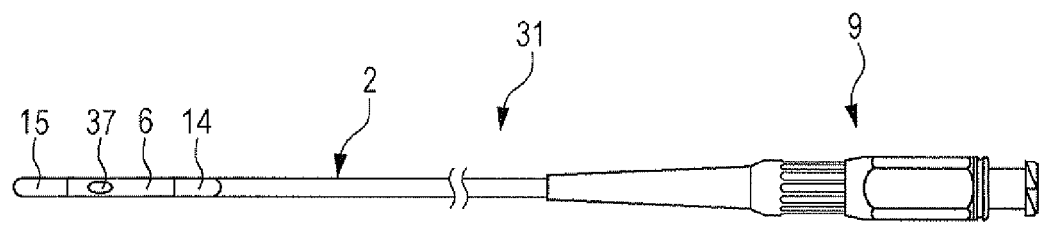
Figure 5C:
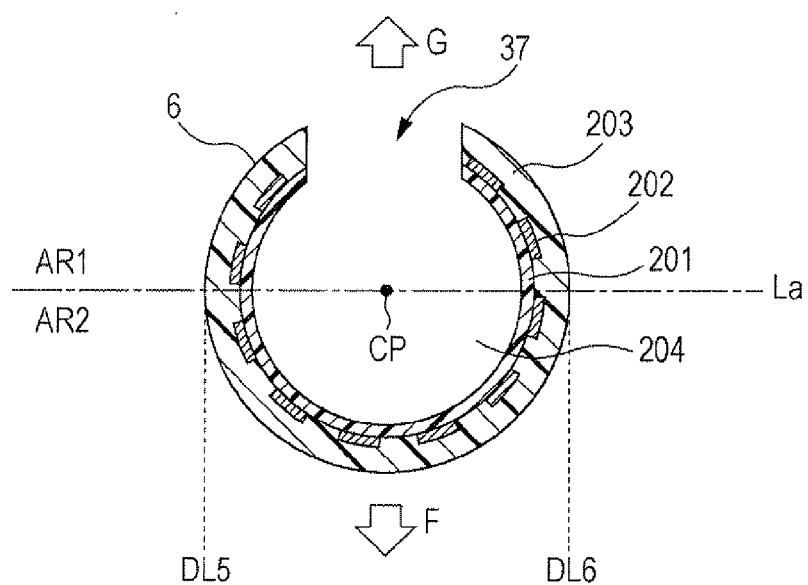

FIGS. 5A to 5C each illustrate the structure of a catheter 31 according to the fourth embodiment. FIG. 5A illustrates the entire catheter 31. FIG. 5B is a plan view of FIG. 5A. FIG. 5C is a transverse sectional view of the catheter 31 taken along line VC-VC in FIG. 5A.

In FIG. 5B, a first curved portion 14, an intermediate portion 6, and a second curved portion 15 of the catheter 31 are provided on a long-axis line of the catheter 31.

In FIG. 5C, in transverse sectional view of the intermediate portion 6, the first curved portion 14 and the second curved portion 15 are curved so as to be positioned between a broken line DL5 and a broken line DL6. Therefore, in transverse sectional view of the intermediate portion 6, a direction of curvature of the first curved portion 14 (hereunder referred to as the "first curvature direction" in the embodiment) and a direction of curvature of the second curved portion 15 (hereunder referred to as the "second curvature direction" in the embodiment) correspond to the direction of arrow F directed towards an AR2 side.

In FIG. 5C, in transverse sectional view of the intermediate portion 6, the second opening portion 37 is provided so as to open in a direction directed towards an opposite side to the side towards which the first curvature direction (that is, the direction of arrow F (an AR2 side)) of the first curved portion 14 and to the second direction of the second curved portion 15 (that is, the direction of arrow F (the AR2 side)) are directed. That is, the second opening portion 37 is provided so as to open in the direction of arrow G (the AR1 side).

As mentioned above, in transverse sectional view of the intermediate portion 6, the second opening portion 37 opens in the direction directed towards the opposite side to the side towards which the first curvature direction of the first curved portion 14 and the second direction of the second curved portion 15 are directed. Therefore, it is possible to considerably improve passibility of a guidewire or a microcatheter through the other coronary artery from the second opening portion 37, and to make it easier for a force that is applied to the catheter 31 to be reliably dispersed to both of the coronary arteries through the guidewire or the microcatheter, the force being generated when a medical device is inserted into the catheter 31. Therefore, it is possible to increase the efficiency of PCI operations, and, thus, to stabilize the form of disposition of the catheter 31.

Next, with reference to FIG. 6, a catheter 41 according to a fifth embodiment is described focusing on the differences between the catheter 41 according to the fifth embodiment and the catheter 1 according to the first embodiment. Portions in the fifth embodiment that correspond to those in the first embodiment are given the same reference numerals in FIG. 6.

Figure 6A:
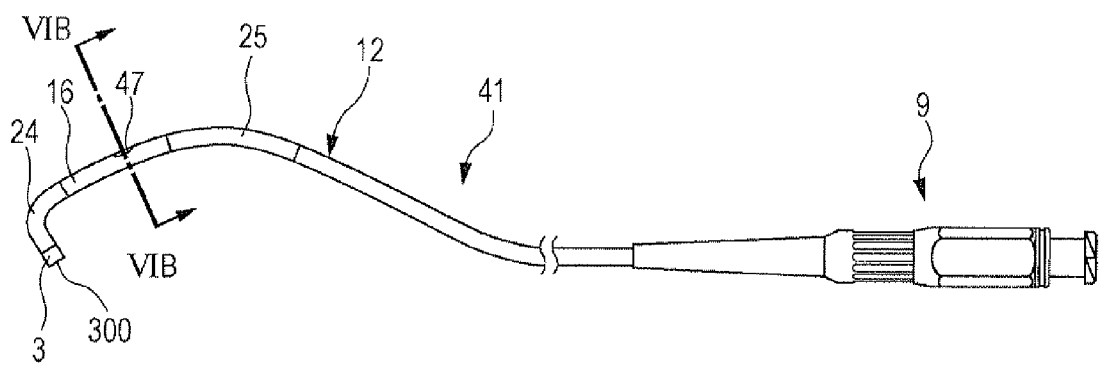
FIGS. 6A and 6B each illustrate the structure of a catheter according to a fifth embodiment, with FIG. 6A illustrating the entire catheter and FIG. 6B being a transverse sectional view of the catheter taken along line VIB-VIB in FIG. 6A.
Figure 6B:
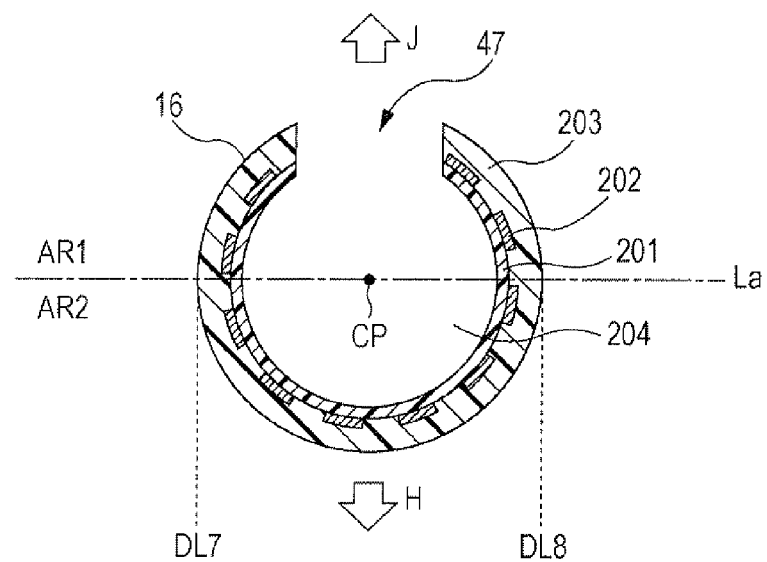

FIGS. 6A and 6B each illustrate the structure of the catheter 41 according to the fifth embodiment. FIG. 6A illustrates the entire catheter 41. FIG. 6B is a transverse sectional view of the catheter 41 taken along line VIB-VIB in FIG. 6A. In order to facilitate understanding, in FIG. 6A, the entire catheter 41 is schematically shown, with the catheter 41 being shortened in a lengthwise direction thereof. Therefore, the overall dimensions differ from the actual dimensions.

In FIG. 6A, the catheter 41 has a distal-end form that differs from that of the catheter 1 according to the first embodiment, and includes a connector 9 and a catheter body 12, which is positioned at a distal end of the connector 9, in that order from a proximal-end of the catheter 41. The catheter body 12 includes, from its tip portion side, a distal-end tip 3, a first curved portion 24, a second curved portion 25, an intermediate portion 16, and a second opening portion 47. The distal-end tip 3 has a first opening portion 300. The first curved portion 24 is positioned at a proximal end of the distal-end tip 3. The second curved portion 25 is positioned proximally of the first curved portion 24. The intermediate portion 16 is positioned between the first curved portion 24 and the second curved portion 25. The second opening portion 47 is formed in the intermediate portion 16. Although not illustrated, as shown in FIG. 5B, the first curved portion 24, the intermediate portion 16, and the second curved portion 25 of the catheter 41 are provided so as to be positioned on a long axis of the catheter 41.

In FIG. 6B, in transverse sectional view of the intermediate portion 16, the first curved portion 24 and the second curved portion 25 are curved so as to be positioned between a broken line DL7 and a broken line DL8. Therefore, a direction of curvature of the first curved portion 24 (hereunder referred to as the "first curvature direction" in the embodiment) and a direction of curvature of the second curved portion 25 (hereunder referred to as the "second curvature direction" in the embodiment) correspond to the direction of arrow H directed towards an AR2 side in transverse sectional view of the intermediate portion 16.

In FIG. 6B, in transverse sectional view of the intermediate portion 16, the second opening portion 47 is provided so as to open in a direction directed towards an opposite side to the side towards which the first curvature direction of the first curved portion 24 (that is, the direction of arrow H (the AR2 side)) and the second curvature direction of the second curved portion 25 (that is, the direction of arrow H (the AR2 side)) are directed. That is, the second opening portion 47 opens in the direction of arrow J (an AR1 side).

Next, the forms of use of the catheter 41 and the advantages that are provided when the catheter 41 according to the embodiment is used are described with reference to FIG. 7.

Figure 7:
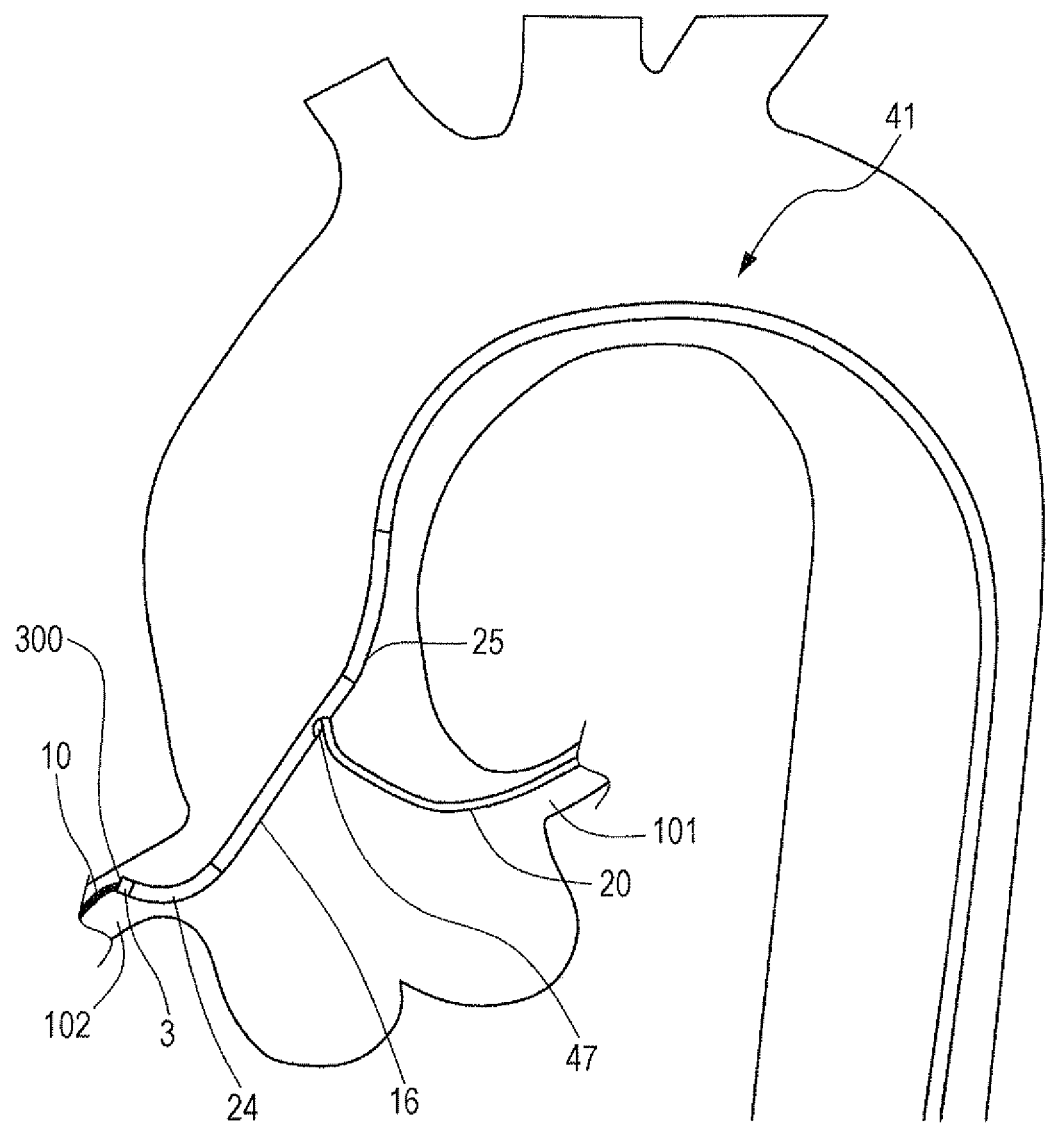
FIG. 7 is an explanatory view of a state in which the catheter according to the fifth embodiment is used.

FIG. 7 illustrates a state in which a distal end (first opening portion 300) of the catheter 41 is inserted in a right coronary artery 102 when it is assumed that an obstructing lesion (not shown) exists in the right coronary artery 102. The catheter 41 is inserted from a patient's femoral artery, and the distal end (first opening portion 300) of the catheter 41 is inserted into the right coronary artery 102 through an aorta 100, to dispose a first medical device 10, such as a guidewire, in the right coronary artery 102 through the first opening portion 300.

In this state, a second medical device 20, such as a microcatheter, is inserted into a left coronary artery 101 through the second opening portion 47, and a contrast medium is caused to flow into the left coronary artery 101 through the microcatheter. This makes it possible to perform contralateral contrastradiography.

As mentioned above, even if the catheter 41 according to the fifth embodiment has a distal end whose form differs from that of the distal end of the catheter 1 according to the first embodiment, since the catheter 41 includes the intermediate portion 16, which is disposed between the first curved portion 24 and the second curved portion 25, and the second opening portion 47, which is formed in the intermediate portion 16, and, since, as mentioned above, in transverse sectional view of the intermediate portion 16, the second opening portion 47 opens in a direction directed towards an opposite side to the side towards which the first curvature direction of the first curved portion 24 and the second curvature direction of the second curved portion 25 are directed, the following is achieved. That is, even in a state in which the first opening portion 300 is inserted in the entrance of one of the coronary arteries (that is, the right coronary artery 102 in FIG. 7), since the second opening portion 47 opens towards the entrance of the other coronary artery (that is, the left coronary artery 101 in FIG. 7), when a microcatheter 20 is disposed in the other coronary artery through the second opening portion 47, it is possible to perform treatment of a lesion of one of the coronary arteries and perform contralateral contrastradiography of the other coronary artery using one catheter. This makes it possible to increase the efficiency of PCI operations, and stabilize the form of insertion of the catheter 41 into the right coronary artery 102.

Next, modifications of the second opening portion are hereunder described with reference to FIGS. 8A to 8D.

FIG. 8A is an enlarged vertical sectional view of an intermediate portion 6 having a second opening portion 57, and FIG. 8C is an enlarged vertical sectional view of an intermediate portion 6 having a second opening portion 67. FIG. 8B is a plan view of FIG. 8A, and FIG. 8D is a plan view of FIG. 8C.

In FIGS. 8A and 8B, the second opening portion 57 includes a first inclined portion 210 that is formed so that the area at an outer surface side of the catheter body 2 is larger than the area at a inner surface side of the catheter body 2 (that is, the side of a lumen 204).

Accordingly, since the area of the outer-surface side of the second opening portion 57 is larger than the area of the inner-surface side of the second opening portion 57, the range of operation when a medical device, such as a guidewire or a microcatheter, is moved towards the entrance of the other coronary artery from the second opening portion 57 is increased, so that it becomes easier to insert the medical device into the other coronary artery, and, thus, it is possible to further increase the efficiency of PCI operations.

In FIGS. 8C and 8D, the second opening portion 67 includes a first inclined portion 210, a second inclined portion 230, and an edge 220. The first inclined portion 210 is inclined towards an inner surface so that the area of its inner-surface side is smaller than the area of its outer-surface side. The second inclined portion 230 is inclined towards an outer surface so that the area of its outer-surface side is smaller than the area of its inner-surface side (the side of the lumen 204). The edge 220 is a portion where the first inclined portion 210 and the second inclined portion 230 contact each other, and is where the area in the second opening portion 67 is smallest. That is, the second opening portion 67 has a form in which the area at a position of the second opening portion 67 between the outer-surface side and the inner-surface side (the side of the lumen 204) of the second opening portion 67 is smaller than the area at the outer-surface side and the area at the inner-surface side of the second opening portion 67.

Accordingly, since the second opening portion 67 has a form in which the area at a position of the second opening portion 67 between the outer-surface side and the inner-surface side of the second opening portion 67 is smaller than the area at the outer-surface side and the area at the inner-surface side of the second opening portion 67, it becomes easier to move out a medical device, such as a guidewire or a microcatheter, from the catheter through the second opening portion 67, and to increase insertability of the medical device into the entrance of the other coronary artery. Therefore, it is possible to considerably increase the efficiency of PCI operations.

Such second openings 57 and 67 are formed by obliquely illuminating the catheter body 2 using a YAG laser.

It is desirable to form the first inclined portion 210 and the second inclined portion 230 so that the area at the outer-surface side at the catheter body 2 is larger than the area of the inner-surface side (the side of the lumen 204) at the catheter body 2.

Since the area at the outer-surface side at the catheter body 2 is larger than the area at the inner-surface side (the side of the lumen 204) at the catheter body 2, it is possible to further increase insertability of a medical device into the entrance of the other coronary artery. Therefore, it is possible to considerably increase the efficiency of PCI operations.

Next, other modifications of the second opening portion are hereunder described with reference to FIGS. 9A and 9B.

Figure 9A:
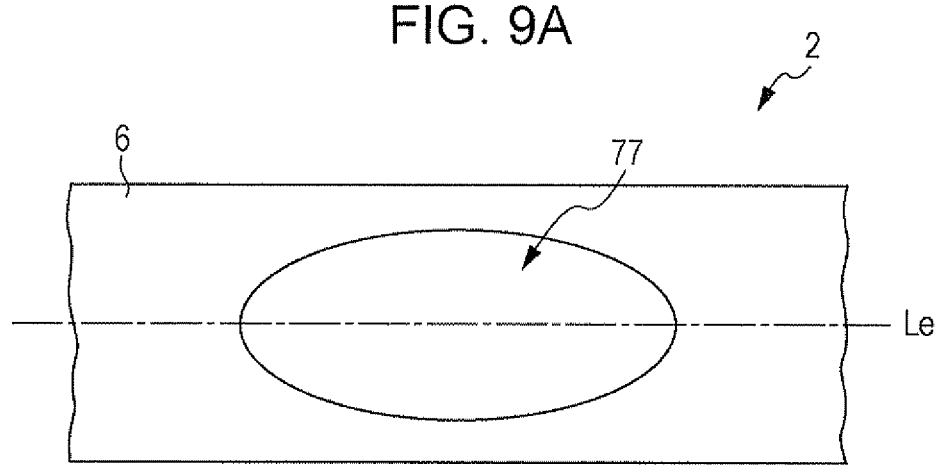
FIG. 9A and 9B are plan views of catheters showing modifications of the second opening portion, with FIG. 9A being a plan view of one modification and FIG. 9B being a plan view of another modification.
Figure 9B:
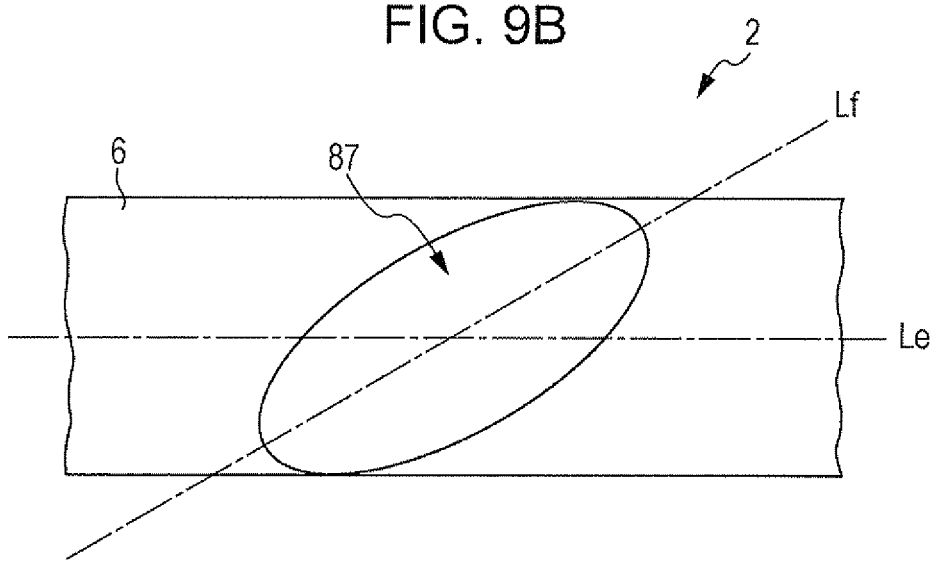

In FIG. 9A, a second opening portion 77 has an elliptical shape. The second opening portion 77 is disposed on an intermediate portion 6 so that a centerline (not shown) of the second opening portion 77 extending along a long-axis direction thereof is superimposed upon a centerline Le of the intermediate portion 6 of the catheter body 2 in a long-axis direction of the intermediate portion In FIG. 9B, a second opening portion 87 has an elliptical shape having a long axis along a direction (line segment Lf) that crosses a long-axis direction (line segment Le) of the intermediate portion 6 of the catheter body 2.

Since the second opening portion 77 has an elliptical shape along the long-axis direction of the catheter body 2, it is possible to smoothly move out a medical device that has been inserted into the catheter from the second opening portion 77. Since the second opening portion 87 has an elliptical shape having a long axis along the direction (line segment Lf) that crosses the long-axis direction (light segment Le) of the intermediate portion 6, it is possible to provide a range of operation of a guidewire or a microcatheter in a direction that crosses the long-axis direction of the intermediate portion 6. Therefore, it is possible to further improve insertability of the medical device into the entrance of the other coronary artery, and to further increase the efficiency of PCI operations.

In particular, it is desirable to use each of the second opening portions 77 and 87 having elliptical shapes in combination with the modifications illustrated in FIGS. 8A to 8D.

By combining the second opening portions 77 and 87 having elliptical shapes with the modifications shown in FIGS. 8A to 8D, it is possible to considerably improve insertability of a medical device, such as a microcatheter, into the other coronary artery. Therefore, it is possible to considerably increase the efficiency of PCI operations.

The present invention is not limited to the above-described embodiments, so that various changes may be made by any person skilled in the art within the technical idea of the present invention.

For example, although the drawings of the disclosed embodiments illustrate the states in which the catheters are inserted from a femoral artery, the present invention is not limited thereto. The catheters may be suitably applied when they are inserted from a brachial artery or radial artery.

As another example, the lengths of the intermediate portions 6 and 16 in the long-axis directions thereof may be as long as, longer, or shorter than the lengths of the corresponding first curved portions 4 and 24 in the long-axis directions thereof and the lengths the second curved portions 5 and 25 in the long-axis directions thereof.

As a further example, in the figures illustrating the disclosed embodiments, the intermediate portions 6 and 16 are linearly formed. The catheter, however, may also include an intermediate portion that is gently curved continuously from the first curved portion towards the second curved portion.

In order to improve the operability of a medical device, such as a microcatheter, at the second opening portion and to improve the insertability of the medical device into the other coronary artery, the frictional resistance between the medical device, such as a microcatheter, and the second opening portion may be reduced by applying a material having a higher lubricity than the resin material of the outer layer 203 to an edge of the second opening portion.

Although the material that may be used as such a material having lubricity is not particularly limited, a hydrophobic coating material (such as silicone oil or fluorocarbon resin), or a hydrophilic coating material (such as polyvinylpyrrolidone, polyacrylic acid, polyacrylamide, polyvinyl alcohol, maleic anhydride copolymer, or hyaluronic acid) may be used.

What is claimed is:

1. A catheter comprising:
   a first opening portion that is positioned at a distal end of the catheter;
   a first curved portion that is positioned proximally of the first opening portion, the first curved portion being curved in a first direction;
   a second curved portion that is positioned proximally of the first curved portion, the second curved portion being curved in a second direction;
   an intermediate portion that is provided between the first curved portion and the second curved portion; and
   a second opening portion that is formed in the intermediate portion, wherein
   in a transverse sectional view of the intermediate portion, the first direction and the second direction are directions directed towards a first side of the intermediate portion,
   in the transverse sectional view of the intermediate portion, the second opening portion opens in a third direction directed towards a second side of the intermediate portion that is opposite to the first side, and
   the second opening portion has a form in which a first area of an outer-surface side of the second opening portion is larger than a second area of an inner-surface side of the second opening portion.

2. The catheter according to claim 1, wherein, in the transverse sectional view of the intermediate portion, the second opening portion is disposed between a line extending in a direction that is opposite to the first direction and a line extending in a direction that is opposite to the second direction.

3. The catheter according to claim 1, wherein,
   in the transverse sectional view of the intermediate portion, the second opening portion is disposed on a line that extends from a line segment in the third direction, the line segment passing midway between the first direction and the second direction.

4. The catheter according to claim 1, wherein the second opening portion has a form in which a third area at a position of the second opening portion between the outer-surface side and the inner-surface side of the second opening portion is smaller than the first area and the second area.

5. The catheter according to claim 1, wherein the second opening portion is located between a proximal end of the intermediate portion and a mid-position of the intermediate portion in a long-axis direction of the intermediate portion.

6. The catheter according to claim 1, wherein the second opening portion has an elliptical shape.

7. The catheter according to claim 6, wherein the elliptical shape of the second opening portion has a long axis along a direction that crosses a long-axis direction of the intermediate portion.

8. The catheter according to claim 1, wherein the first and second directions are directed in a same direction, and the third direction is directed opposite of the first and second directions.

9. The catheter according to claim 1, further comprising:
   an inner layer defining a lumen;
   a reinforcing body disposed outside of the inner layer; and
   an outer layer disposed outside of the inner layer and the reinforcing body, wherein
   the lumen extends over the entire length of the catheter.

* * * * *